(12) United States Patent
Kawasaki

(10) Patent No.: US 9,789,230 B2
(45) Date of Patent: *Oct. 17, 2017

(54) MEDICAL GUIDE WIRE

(75) Inventor: Hironori Kawasaki, Tokyo (JP)

(73) Assignee: JAPAN LIFELINE CO., LTD., Tokyo (JP)

( * ) Notice: Subject to any disclaimer, the term of this patent is extended or adjusted under 35 U.S.C. 154(b) by 1143 days.

This patent is subject to a terminal disclaimer.

(21) Appl. No.: 13/265,947

(22) PCT Filed: Feb. 9, 2010

(86) PCT No.: PCT/JP2010/051860
§ 371 (c)(1),
(2), (4) Date: Oct. 24, 2011

(87) PCT Pub. No.: WO2010/134364
PCT Pub. Date: Nov. 25, 2010

(65) Prior Publication Data
US 2012/0059279 A1  Mar. 8, 2012

(30) Foreign Application Priority Data

May 20, 2009  (JP) ................................ 2009-121810
Sep. 15, 2009  (JP) ................................ 2009-212621

(51) Int. Cl.
*A61M 25/09* (2006.01)
*A61L 31/02* (2006.01)

(52) U.S. Cl.
CPC ............ *A61L 31/022* (2013.01); *A61M 25/09* (2013.01); *A61M 2025/09083* (2013.01);
(Continued)

(58) Field of Classification Search
CPC ........ A61M 25/09; A61M 2025/09083; A61M 2025/09133; A61M 2025/09166; A61M 2025/09175; A61L 31/022
(Continued)

(56) References Cited

U.S. PATENT DOCUMENTS 5,147,317 A  9/1992 Shank et al.
5,234,003 A  8/1993 Hall
(Continued)

FOREIGN PATENT DOCUMENTS

EP  1123714 A1  8/2001
EP  2014329 A1  1/2009
(Continued)

OTHER PUBLICATIONS

Jacobson, et al. (2005). Principles of Brazing. ASM International. Sect. 5.4. pp. 197-200. Retrieved from <http://app.knovel.com/hotlink/toc/id:kpPB000004/principles-brazing/principles-brazing> on Jan. 12, 2015.*
(Continued)

*Primary Examiner* — David J McCrosky
(74) *Attorney, Agent, or Firm* — Holtz, Holtz & Volek PC

(57) ABSTRACT

A medical guide wire including a core wire having a distal end-side small-diameter portion and a proximal end-side large-diameter portion, and a coil spring installed on an outer periphery of the distal end-side small-diameter portion of the core wire along an axial direction, having a front end-side small-diameter portion, a tapered portion and a rear end-side large-diameter portion, and fixed to the core wire, wherein the front end-side small-diameter portion of the coil spring has a length of 5 to 100 mm, and the outside diameter of a coil thereof is at most 0.012 inch, the front end portion of the coil spring is fixed to the core wire by a gold-containing solder, and a length of a distal end portion stiffened by the gold-containing solder is 0.1 to 0.5 mm.

13 Claims, 5 Drawing Sheets

(52) U.S. Cl.
  CPC ............. *A61M 2025/09091* (2013.01); *A61M 2025/09133* (2013.01); *A61M 2025/09166* (2013.01); *A61M 2025/09175* (2013.01)

(58) Field of Classification Search
  USPC ...................................... 148/23, 24; 403/272
  See application file for complete search history.

(56) References Cited

U.S. PATENT DOCUMENTS

| | | | |
|---|---|---|---|
| 6,251,086 B1* | 6/2001 | Cornelius | A61M 25/09 600/585 |
| 6,669,652 B2* | 12/2003 | Anderson | A61M 25/09 600/434 |
| 7,170,100 B2 | 1/2007 | Erchak et al. | |
| 7,637,874 B2* | 12/2009 | Terashi et al. | 600/585 |
| 7,993,286 B2 | 8/2011 | Reynolds et al. | |
| 2007/0249964 A1 | 10/2007 | Richardson et al. | |
| 2007/0282225 A1* | 12/2007 | Terashi | A61M 25/09 600/585 |
| 2008/0033530 A1* | 2/2008 | Zberg et al. | 420/402 |
| 2008/0097248 A1 | 4/2008 | Munoz et al. | |
| 2008/0146967 A1 | 6/2008 | Richardson et al. | |
| 2008/0281230 A1 | 11/2008 | Kinoshita et al. | |
| 2008/0292493 A1* | 11/2008 | Lee et al. | 420/561 |
| 2011/0319872 A1 | 12/2011 | Kawasaki | |

FOREIGN PATENT DOCUMENTS

| | | |
|---|---|---|
| JP | 2003-299739 A | 10/2003 |
| JP | 2006-020942 A | 1/2006 |
| JP | 2006-055245 A | 3/2006 |
| JP | 2006-223728 A | 8/2006 |
| JP | 2007-111118 A | 5/2007 |
| JP | 2008-307367 A | 12/2008 |
| JP | 4354525 B1 | 8/2009 |
| JP | 2010-268888 A | 2/2010 |
| JP | 2010-214054 A | 9/2010 |
| WO | WO 2008/022126 A1 | 2/2008 |
| WO | WO 2010/134364 A1 | 11/2010 |

OTHER PUBLICATIONS

Machine translation of JP2006-020942.*
English-language International Preliminary Report on Patentability and Written Opinion of the International Searching Authority dated Dec. 12, 2011 for PCT/JP2010/051860 filed Feb. 9, 2010; Applicant: Japan Lifeline Co., Ltd.
D.R. Olsen et al., "Properties of Die Bond Alloys Relating to Thermal Fatigue", *IEEE Transactions on Components, Hybrids, and Manufacturing Technology*, vol. CHMT-2, No. 2, Jun. 1979.
Abstract XP002719332 of JP H0 7234338, Hitachi Ltd., Sep. 5, 1995.
Thomson Scientific Abstract of JP 2006-020942, Terumo Corp., Jan. 26, 2006.
Third Office Action (Written Notification of Reason for Refusal) dated Mar. 27, 2014 for corresponding Chinese application 201080010146.4 (including an English-language translation thereof).
Japanese Office Action dated Jan. 18, 2013 in Japanese patent application 2009-212621.
Chinese Office Action dated Feb. 5, 2013 in Chinese patent application 201080010146.4.
Supplementary European Search Report dated Oct. 26, 2012 for EP 10 77 7600.
Second Office Action dated Sep. 30, 2013 for corresponding Chinese application 201080010146.4 (including an English-language translation).
Chinese Office Action dated Aug. 12, 2014, issued in counterpart Chinese Application No. 201080010146.4.
Australian Office Action dated Oct. 17, 2014, issued in counterpart Australian Application No. 2010250563.

* cited by examiner

FIG. 4
(A)
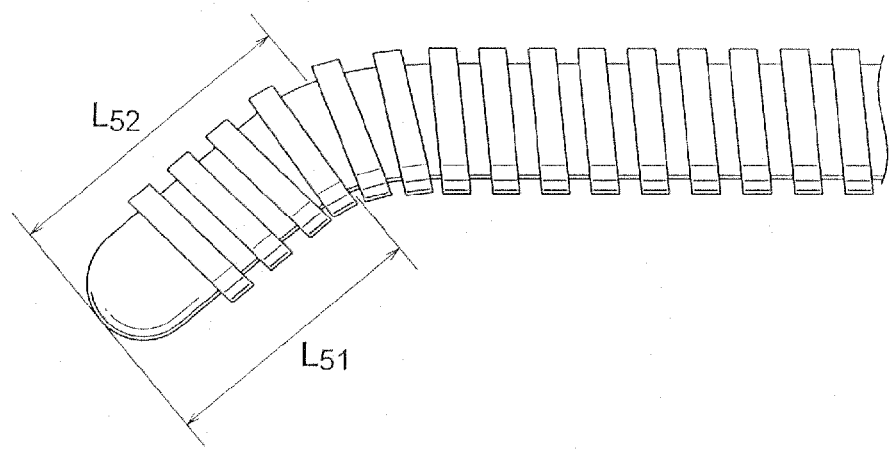
(B)
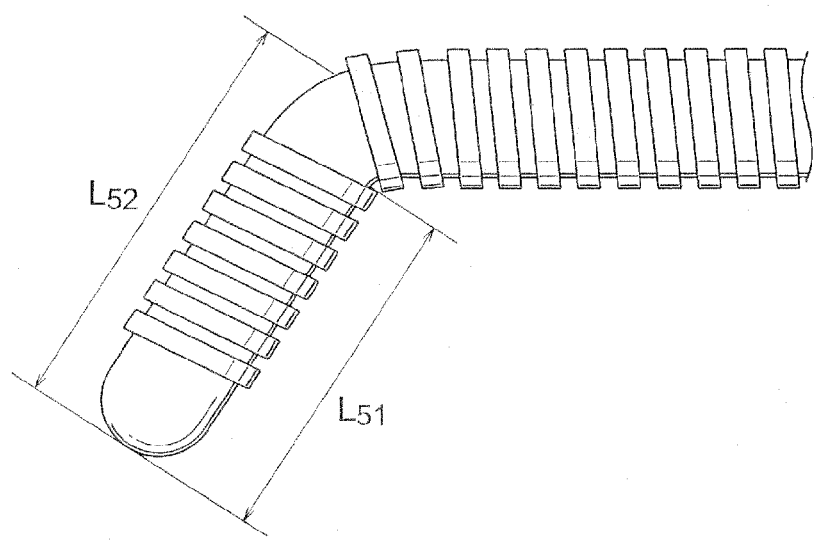

MEDICAL GUIDE WIRE

CROSS-REFERENCE TO RELATED APPLICATION

This application is a United States national phase application of International Application PCT/JP2010/051860 filed Feb. 9, 2010.

TECHNICAL FIELD

The present invention relates to a medical guide wire having a coil spring installed on an outer periphery of a distal end-side small-diameter portion of a core wire, and more particularly to a medical guide wire which is high in fixing strength of a coil spring to a core wire, can more shorten a shaping length in a shaping operation at a distal end portion than a conventional one and has high flexural rigidity and excellent torque transmissibility.

BACKGROUND ART

A guide wire for guiding a medical instrument such as a catheter to a predetermined position in a body cavity such as a blood vessel is required to have flexibility at its distal end portion.

Therefore, there is known a guide wire in which the outside diameter of an distal end portion of a core wire is made smaller than that of its proximal end portion, and a coil spring is installed on an outer periphery of the distal end portion (distal end-side small-diameter portion) of the core wire, thereby intending to improve the flexibility of the distal end portion (see, for example, Patent Literature 1).

In order to install the coil spring on the outer periphery of the distal end-side small-diameter portion of the core wire, both front end portion and rear end portion of the coil spring are generally fixed to the core wire by solder.

Here, Ag—Sn solder is used as the solder for fixing both front end portion and rear end portion of the coil spring to the core wire because of its low melting point and easy handling.

The solder penetrated into the interior of the coil at both front end portion and rear end portion of the coil spring comes into contact with the outer peripheral surface of the core wire, whereby the coil spring is fixed to the core wire.

In addition, a distal end tip is formed by any other solder than the solder penetrated into the interior of the coil at the front end portion of the coil spring.

In order to ensure the fixing ability of the coil spring to the core wire, however, it is necessary to sufficiently penetrate the solder into the interior of the coil at the front end portion of the coil spring, which is fixed to a distal end portion of the core wire, which has a minimum outside diameter. Specifically, it is necessary to penetrate the solder (Ag—Sn solder) into the interior of the coil in a range corresponding to about 6 pitches to about 8 pitches of the coil spring.

A portion (including the distal end tip formed by the solder) stiffened by the solder filled into the interior of the coil is formed at the distal end portion of the guide wire produced in this manner.

The length (length corresponding to the distal end tip and about 6 pitches to about 8 pitches of the coil) of this distal-end stiff portion is about 0.8 to 1.1 mm.

In order to achieve low invasiveness in a patient, it has been recently desired to miniaturize medical instruments.

With this desire, there has been a demand for making the diameter of a guide wire small, and so the present inventors have developed a guide wire having a smaller wire diameter (0.010 inch) than that (0.014 inch) of a conventional one.

The guide wire of 0.010 inch can greatly contribute to the miniaturization of medical instruments such as catheters.

In addition, this guide wire is also good in operability upon accessing, for example, a micro-channel in CTO (chronic total occlusion) lesion.

CITATION LIST

Patent Literature

Patent Literature 1: Japanese Patent Application Laid-Open No. 2003-299739

SUMMARY OF INVENTION

Technical Problem

The guide wire inserted into the micro-channel in the CTO lesion is required to improve the operability further. For example, it is desired to reduce a frictional resistance upon operation within the micro-channel. However, there is a limit to the reduction of the frictional resistance by making the wire diameter of the guide wire small.

By the way, an operator shapes (shaping) a distal end portion of a guide wire into a bent portion when the guide wire is inserted into the micro-channel.

For example, when the shaping is conducted by bending the guide wire G by 45° at a position 1.0 mm away from the distal end thereof as illustrated in FIG. 5, and rotational torque is applied to the guide wire on its proximal end side, the distal end of the guide wire comes to be rotated on a circumference having a diameter of about 1.4 mm.

This shaping operation greatly affects the operability of the guide wire within the micro-channel.

The diameter (operation area) of a circle drawn by the rotation of the distal end of the guide wire is preferably made small from the viewpoint of, for example, reducing the frictional resistance within the micro-channel. It is thus necessary to make a shaping length (length of the bent portion on the distal end side) as short as possible, specifically, not more than 0.7 mm.

However, the conventional guide wire has the above-described distal-end stiff portion, and so the shaping length cannot be set to 1.0 mm or less, thereby failing to sufficiently reduce the frictional resistance.

Incidentally, if the length of the distal-end stiff portion is shortened by narrowing a range where the solder (Ag—Sn solder) is penetrated, the fixing ability of the coil spring to the core wire cannot be sufficiently ensured, and the core wire in a state inserted into the coil spring is pulled out from the coil spring when tensile force is applied between the core wire and the coil spring.

On the other hand, the guide wire having a diameter as fine as 0.010 inch does not have sufficient flexural rigidity, so that such a guide wire is poor in pushability upon insertion and also involves a problem that the guide wire is liable to bend when a device is delivered after the insertion, and is poor in delivery performance. The fine-diameter guide wire is also poor in torque transmissibility.

The present invention has been made on the basis of the foregoing circumstances.

The first object of the present invention is to provide a medical guide wire which is high in fixing strength of a coil spring to a core wire and can shorten a shaping length compared with a conventional one.

The second object of the present invention is to provide a medical guide wire excellent in operability within a micro-channel of CTO lesion.

The third object of the present invention is to provide a medical guide wire which has sufficient flexural rigidity and is also excellent in torque transmissibility though it is low in invasiveness and good in operability upon accessing a micro-channel.

Solution to Problem

A medical guide wire according to the present invention comprises a core wire having a distal end-side small-diameter portion and a proximal end-side large-diameter portion having a larger outside diameter than the outside diameter of the distal end-side small-diameter portion, and a coil spring installed on an outer periphery of the distal end-side small-diameter portion of the core wire along an axial direction, having a front end-side small-diameter portion, a rear end-side large-diameter portion having a larger outside diameter of coil than that of the front end-side small-diameter portion and a tapered portion located between the front end-side small-diameter portion and the rear end-side large-diameter portion, and fixed to the core wire at least the front end portion and rear end portion thereof, wherein the length of the front end-side small-diameter portion of the coil spring is 5 to 100 mm, and the outside diameter of coil thereof is at most 0.012 inch, the front end portion of the coil spring is fixed to the core wire by gold-containing solder, and the length of a distal-end stiff portion by the gold-containing solder is 0.1 to 0.5 mm.

Here, "the gold-containing solder" includes Au alloy solder such as Au—Sn solder, Au—Ge solder, Au—Si solder, Au—In solder and Au—Sb solder, and Au solder.

A medical guide wire according to a preferred embodiment of the present invention comprises a core wire having a distal end-side small-diameter portion and a proximal end-side large-diameter portion having a larger outside diameter than the outside diameter of the distal end-side small-diameter portion, and a coil spring installed on an outer periphery of the distal end-side small-diameter portion of the core wire along an axial direction, having a front end-side small-diameter portion, a rear end-side large-diameter portion having a larger outside diameter of coil than that of the front end-side small-diameter portion and a tapered portion located between the front end-side small-diameter portion and the rear end-side large-diameter portion, and fixed to the core wire at least the front end portion and rear end portion thereof, wherein the length of the front end-side small-diameter portion of the coil spring is 5 to 100 mm, and the outside diameter of coil thereof is at most 0.012 inch, the front end portion of the coil spring is fixed to the core wire by Au—Sn solder, and the length of a distal-end stiff portion by the Au—Sn solder is 0.1 to 0.5 mm.

A medical guide wire according to another preferred embodiment of the present invention comprises a core wire having a distal end-side small-diameter portion and a proximal end-side large-diameter portion having a larger outside diameter than the outside diameter of the distal end-side small-diameter portion, and a coil spring installed on an outer periphery of the distal end-side small-diameter portion of the core wire along an axial direction, having a front end-side small-diameter portion, a rear end-side large-diameter portion having a larger outside diameter of coil than that of the front end-side small-diameter portion and a tapered portion located between the front end-side small-diameter portion and the rear end-side large-diameter portion, and fixed to the core wire at least the front end portion and rear end portion thereof, wherein the length of the front end-side small-diameter portion of the coil spring is 5 to 100 mm, and the outside diameter of coil thereof is at most 0.012 inch, the front end portion of the coil spring is fixed to the core wire by Au—Ge solder, and the length of a distal-end stiff portion by the Au—Ge solder is 0.1 to 0.5 mm.

Here, "the distal-end stiff portion" means a front (distal) end portion of the coil spring (guide wire), which cannot be freely bent due to the solder penetrated into the interior of the coil. When a distal end tip is formed by the solder, this distal end tip also becomes a part of the distal-end stiff portion.

In addition, "the length of the distal-end stiff portion" means a length of the guide wire from the distal end of the guide wire to the rear end of the solder penetrated into the interior of the coil in an axial direction.

In the medical guide wire according to the present invention, the following embodiments are preferred.

(1) The outside diameter of coil of the front end-side small-diameter portion of the coil spring is at most 0.010 inch, particularly, 0.006 to 0.010 inch.

(2) The outside diameter of the proximal end-side large-diameter portion of the core wire and the outside diameter of coil of the rear end-side large-diameter portion of the coil spring are each at least 0.014 inch.

(3) The coil pitch of the coil spring at its front end-side small-diameter portion is 1.0 to 1.8 times as much as the wire diameter of the coil, and the Au—Sn solder or Au—Ge solder penetrates into the interior of the coil in a range corresponding to 1 to 3 pitches of the coil spring.

(4) A resin is filled into the interior (space surrounded by the outer periphery of the distal end-side small-diameter portion of the core wire and the inner periphery of the coil spring) of the coil spring, a resin layer by the resin is formed on the outer periphery of the coil spring, a hydrophilic resin layer is laminated and formed on the surface of the resin layer, and a water-repellent resin layer is formed on the surface of the core wire.

(5) In the case of the embodiment (4), the outer periphery of the coil spring including the tapered portion is covered with the resin layer and the hydrophilic resin layer, whereby a taper as a form of the guide wire is formed, and the taper angle of this taper is smaller than that of the tapered portion of the coil spring.

(6) The coil spring is composed of a front end-side densely-coiled portion whose coil pitch is 1.0 to 1.8 times as much as the wire diameter of the coil, and a rear end-side roughly-coiled portion whose coil pitch exceeds 1.8 times as much as the wire diameter of the coil.

(7) In the case of the embodiment (6), the front end-side small-diameter portion and tapered portion are formed by the front end-side densely-coiled portion of the coil spring, and the rear end-side large-diameter portion is formed by the rear end-side roughly-coiled portion of the coil spring.

(8) The core wire is composed of stainless steel.

Advantageous Effects of Invention

According to the medical guide wires of the present invention, the gold-containing solder, preferably, Au—Sn solder or Au—Ge solder is used as solder for fixing the front end portion of the coil spring to the core wire, so that the fixing strength of the coil spring to the core wire can be made sufficiently high (higher than the breaking strength of the distal end-side small-diameter portion of the core wire) though the length of the distal-end stiff portion is as short (narrow in a region fixed by the solder) as 0.1 to 0.5 mm, and so the core wire is not pulled out from the coil spring when tensile force is applied to the core wire in a state inserted into the coil spring.

In addition, since the length of the distal-end stiff portion is as short as 0.1 to 0.5 mm, the shaping length (length of the bent portion on the distal end side) can be made short (not more than 0.7 mm). As a result, frictional resistance upon operation within the micro-channel can be sufficiently reduced.

Further, a treatment in a narrow region, which has been unable to be conducted by using the conventional guide wire, also becomes feasible.

The medical guide wires according to the present invention are excellent in operability within the micro-channel of CTO lesion because of the outside diameter of coil as fine as 0.012 inch or less in the front end-side small-diameter portion, high fixing strength owing to the gold-containing solder and the distal-end stiff portion as short as 0.1 to 0.5 mm.

The coil spring making up the medical guide wire according to the present invention has the rear end-side large-diameter portion having a larger outside diameter of coil than that of the front end-side small-diameter portion, whereby good flexural rigidity is ensured, and so such a guide wire becomes excellent in torque transmissibility.

According to the medical guide wire of the above embodiment (4), the resin is filled into the interior of the coil spring, so that the integrity of the core wire with the coil spring is especially improved, whereby the torque transmissibility and operability of the guide wire can be improved further.

In addition, since the hydrophilic resin layer is laminated and formed on the outer periphery of the coil spring through a resin layer by the same resin as that filled into the interior of the coil spring, the hydrophilic resin layer can be surely fixed to stably develop the lubricating ability by the hydrophilic resin.

Further, the water-repellent resin layer is formed on the surface of the core wire, whereby a blood of a patient can be prevented from coming into contact with a metal making up the core wire to cause an allergy, and the adhesion of the blood can be surely prevented by the water-repellent resin layer. In addition, lubricating ability to other medical instruments can be developed.

According to the medical guide wire of the above embodiment (5), the taper having a smaller taper angle (gentler slope) than that of the tapered portion of the coil spring is formed as the form of the guide wire, whereby the insertion operation of the guide wire can be more smoothly conducted.

According to the medical guide wire of the above embodiment (6) [the embodiment (7)], good contrasting characteristic for X-ray (visibility) can be developed at the front end-side densely-coiled portion (front end-side small-diameter portion and tapered portion) of the coil spring.

BRIEF DESCRIPTION OF DRAWINGS

FIG. 4 is a side elevation illustrating a state that the distal end portion of the guide wire has been shaped.

DESCRIPTION OF EMBODIMENTS

Figure 1:
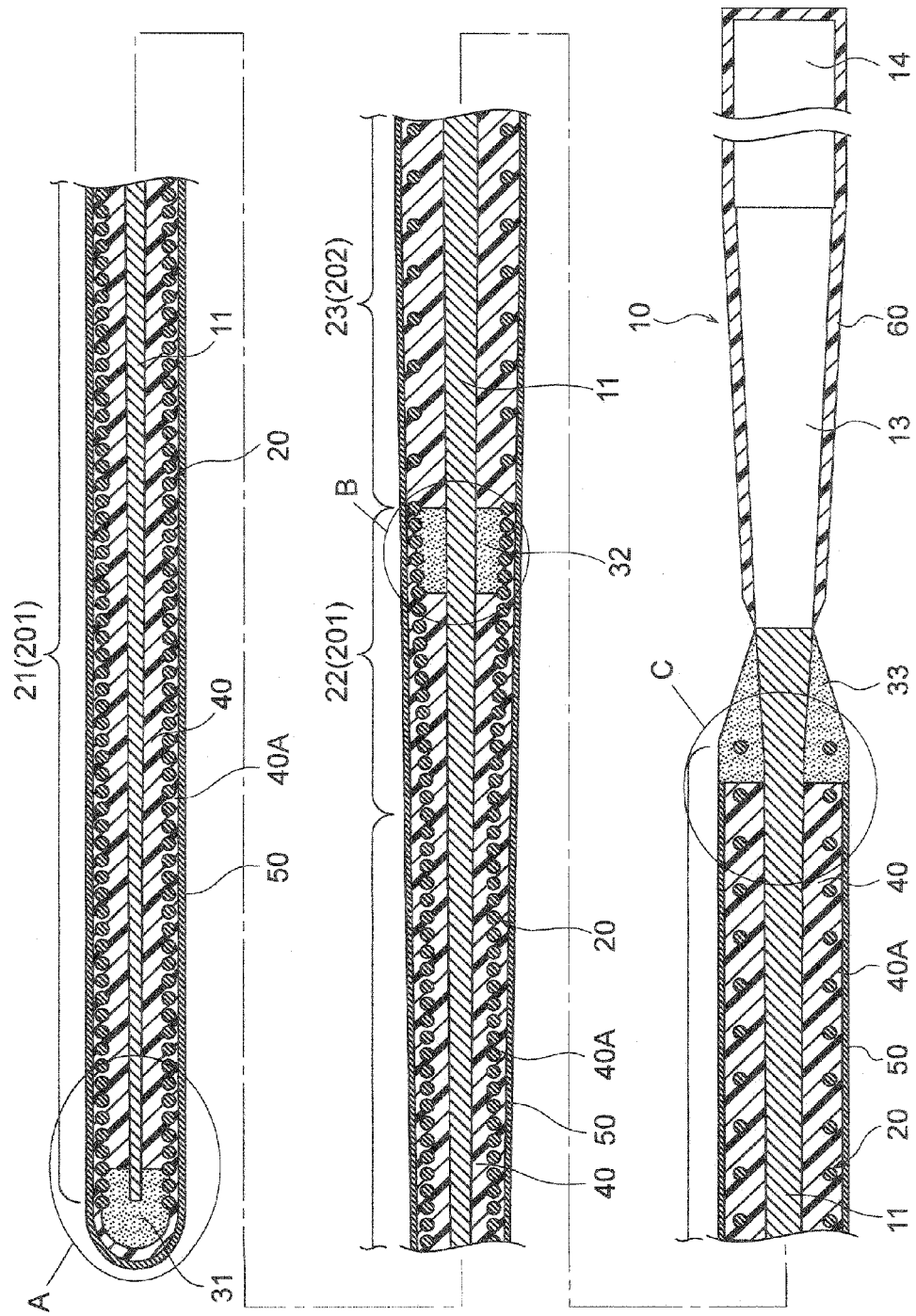
FIG. 1 is a side elevation, partly broken away, illustrating a guide wire according to an embodiment of the present invention.

The guide wire illustrated in FIG. 1 has a core wire 10 and a coil spring 20.

The core wire 10 has a distal end-side small-diameter portion 11 subjected to taper machining so as to expand its diameter towards proximal direction, a tapered portion 13 whose diameter expands towards proximal direction, and a proximal end-side large-diameter portion 14.

The distal end-side small-diameter portion 11, the tapered portion 13 and the proximal end-side large-diameter portion 14 are integrally formed by the same wire material (for example, a round bar member).

The sectional surfaces (cross sections) of the tapered portion 13 and the proximal end-side large-diameter portion 14 are substantially circular.

The sectional surface on a proximal end side of the distal end-side small-diameter portion 11 is substantially circular. However, the wire material may be compressed into a plate form on a distal end side of the distal end-side small-diameter portion 11, and the sectional surface thereof is substantially rectangular in that case.

No particular limitation is imposed on the material of the core wire 10. As examples thereof, however, may be mentioned metals such as stainless steel (for example, SUS316 and SUS304), gold, platinum, aluminum, tungsten, tantalum and alloys thereof. In this embodiment, the core wire is composed of stainless steel.

A water-repellent resin layer 60 is formed on the outer periphery of the core wire 10.

As a resin forming the water-repellent resin layer, may be used all resins medically used and having water repellency, and fluororesins such as PTFE may be mentioned as preferable resins.

Figure 2:
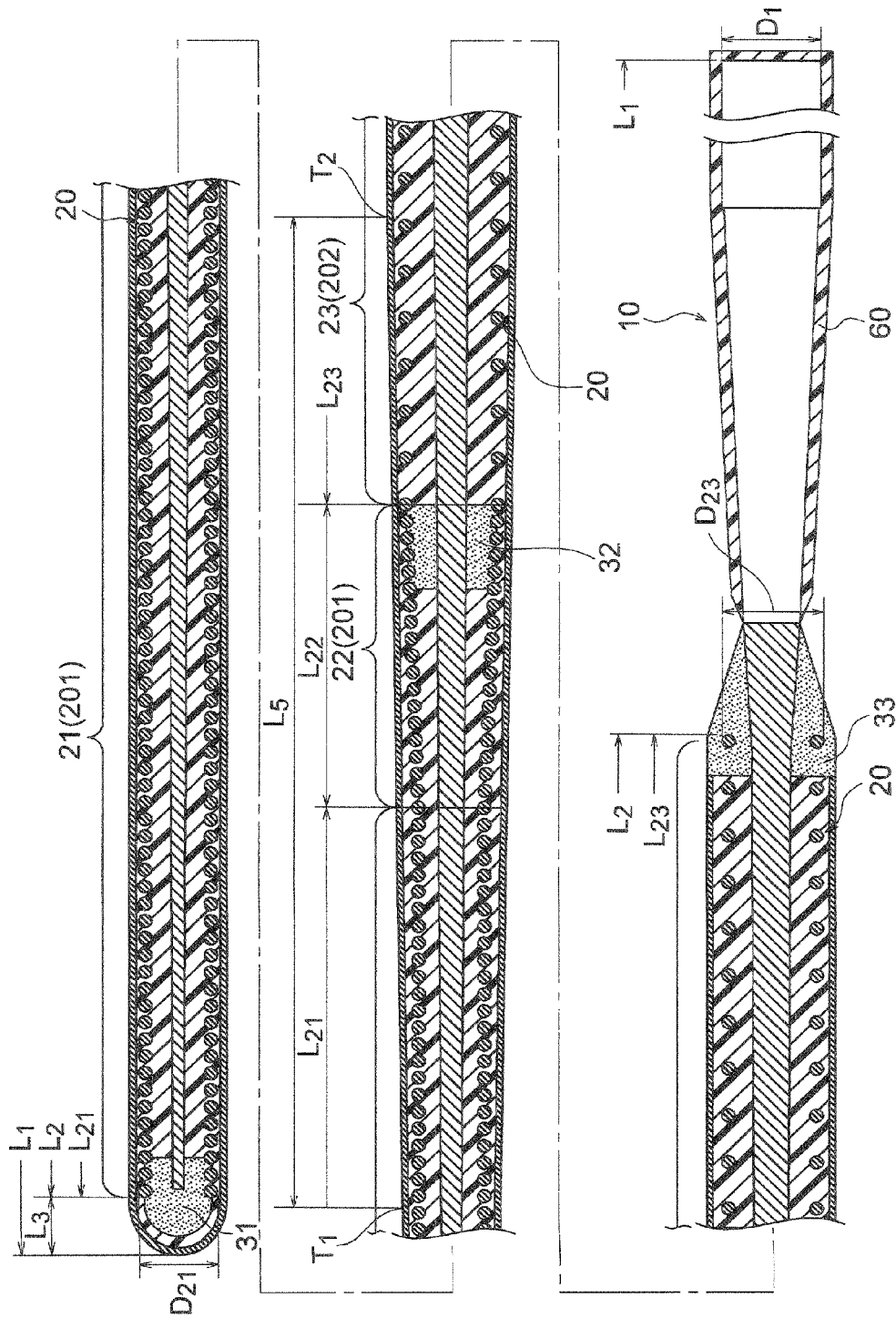
FIG. 2 is a side elevation (drawing for explaining dimensions), partly broken away, illustrating the guide wire according to the embodiment of the present invention.

As illustrated in FIG. 2, the overall length ($L_1$) of the guide wire is, for example, 1,500 to 3,000 mm, and is 1,780 mm as a preferable example.

The outside diameter ($D_1$) of the proximal end-side large-diameter portion 14 of the core wire 10 is preferably 0.014 inch (0.356 mm) or more, and is 0.014 inch as a preferable example.

No particular limitation is imposed on the maximum outside diameter of the distal end-side small-diameter portion 11 so far as it is smaller than the inside diameter of the coil spring 20. However, the outside diameter is preferably about 1/5 to 3/5 of the outside diameter ($D_1$) of the proximal end-side large-diameter portion 14.

The coil spring 20 making up the guide wire is formed by one wire material and installed on an outer periphery of the distal end-side small-diameter portion 11 of the core wire 10 along an axial direction.

The coil spring 20 is composed of a front end-side small-diameter portion 21, a tapered portion 22 and a rear end-side large-diameter portion 23.

In this embodiment, the front end-side small-diameter portion 21 and the tapered portion 22 is formed from a front end-side densely-coiled portion 201, and the rear end-side large-diameter portion 23 is formed from a rear end-side roughly-coiled portion 202. In addition, a radiopaque region is formed by the front end-side densely-coiled portion 201 (the front end-side small-diameter portion 21 and the tapered portion 22) and a distal end tip which will be described hereinafter.

The coil pitch at the front end-side densely-coiled portion 201 is 1.0 to 1.8 times as much as the wire diameter of the coil, and is 1.3 times as a preferable example.

The coil pitch at the rear end-side roughly-coiled portion 202 is 1.8 to 3.0 times as much as the wire diameter of the coil, and is 3.0 times as a preferable example.

The coil pitch is changed between the front end side and the rear end side as described above, whereby good contrasting characteristic for X-ray (visibility) can be developed at the front end-side densely-coiled portion 201.

When the pitch of the coil spring is made same over the whole region, lowering of the visibility is incurred because the radiopaque region becomes long.

In FIG. 2, the length ($L_2$) of the coil spring 20 is, for example, 30 to 800 mm, preferably 100 to 200 mm, and is 165 mm as a preferable example.

The length ($L_{21}$) of the front end-side small-diameter portion 21 is 5 to 100 mm, preferably 10 to 70 mm, and is 38.5 mm as a preferable example.

The length ($L_{21}$) of the front end-side small-diameter portion 21 is 5 mm or more, whereby the front end-side small-diameter portion 2 can be inserted through into almost all micro-channels.

The length ($L_{21}$) of the front end-side small-diameter portion 21 is 100 mm or less, whereby the length of the rear end-side large-diameter portion 23 contributing to improvement in flexural rigidity and torque transmissibility can be enough ensured.

The length ($L_{22}$) of the tapered portion 22 is, for example, 0.5 to 10 mm, and is 1.5 mm as a preferable example.

The length ($L_{23}$) of the rear end-side large-diameter portion 23 is, for example, 85 to 154.5 mm, and is 125 mm as a preferable example.

The length ($L_3+L_2$) from the distal end of the guide wire to the rear end of the coil spring 20 is, for example, 30 to 800 mm, and is 165.2 mm as a preferable example.

The length ($L_3+L_{21}+L_{22}$) from the distal end of the guide wire to the rear end of the tapered portion 22 is, for example, 10 to 50 mm, and is 40.2 mm as a preferable example.

The outside diameter ($D_{21}$) of coil at the front end-side small-diameter portion 21 of the coil spring 20 is generally 0.012 inch (0.305 mm) or less, preferably 0.010 inch (0.254 mm) or less, more preferably 0.006 to 0.010 inch, and is 0.010 inch as a preferable example.

The outside diameter ($D_{21}$) of coil at the front end-side small-diameter portion 21 is 0.012 inch or less, whereby the operability upon accessing a micro-channel (for example, lubricating ability in the micro-channel) becomes excellent.

The outside diameter ($D_{23}$) of coil at the rear end-side large-diameter portion 23 of the coil spring 20 is preferably 0.014 inch (0.356 mm) or more, and is 0.014 inch as a preferable example.

The outside diameter ($D_{23}$) of coil at the rear end-side large-diameter portion 23 is 0.014 inch or more, whereby sufficient flexural rigidity (pushability upon insertion, delivery performance for device after insertion) is imparted to the guide wire, and this guide wire (guide wire according to this embodiment) also becomes excellent in torque transmissibility.

A ratio ($D_{23}/D_{21}$) between the outside diameters of coil of the rear end-side large-diameter portion 23 and the front end-side small-diameter portion 21 is preferably 1.1 to 2.3, and is 1.4 as a preferable example.

No particular limitation is imposed on the outside diameter of the wire material forming the coil spring 20. However, the outside diameter thereof is preferably 30 to 90 µm, and is 60 µm as a preferable example.

As example of the material of the coil spring 20, may be mentioned materials (radiopaque materials) good in contrasting characteristic for X-ray, such as platinum, platinum alloys (for example, Pt/W=92/8), gold, gold-copper alloys, tungsten and tantalum.

In the guide wire according to the present invention, the front end-side small-diameter portion 21, tapered portion 22 and rear end-side large-diameter portion 23 of the coil spring 20 are respectively fixed to the outer periphery of the distal end-side small-diameter portion 11 of the core wire 10 by solder.

As illustrated in FIG. 1 and FIG. 3(A), the front end portion of the front end-side small-diameter portion 21 that is the front end portion of the coil spring 20 is fixed to the core wire 10 by the Au—Sn solder 31.

In short, the Au—Sn solder 31 penetrates into the interior of the front end portion (front end portion of the front end-side small-diameter portion 21) of the coil spring 20 and comes into contact with the outer periphery of the core wire 10 (distal end-side small-diameter portion 11), whereby the front end portion of the coil spring 20 is fixed to the core wire 10 (distal end-side small-diameter portion 11).

As illustrated in FIG. 3(A), the Au—Sn solder 31 penetrates into the interior of the coil in a range corresponding to almost 2 pitches of the coil spring 20.

In addition, a substantially semispherical distal end tip is formed by any other Au—Sn solder 31 than the solder penetrated into the interior of the coil spring 20 at the front end portion of the coil spring 20.

A distal-end stiff portion [stiff portion by the front end portion of the coil spring 20 (front end-side small-diameter portion 21) that has been unable to be freely bent due to the Au—Sn solder 31 penetrated into the interior of the coil, and the distal end tip formed by the Au—Sn solder 31) by the Au—Sn solder 31] is thereby formed at the distal end portion of the guide wire according to this embodiment.

The length (length from the distal end of the guide wire to the rear end of the Au—Sn solder 31 penetrated into the interior of the coil) ($L_4$) of this distal-end stiff portion is about 0.3 to 0.4 mm.

In the guide wire according to the present invention, the length of the distal-end stiff portion is 0.1 to 0.5 mm.

If the length of the distal-end stiff portion is less than 0.1 mm, the fixing ability of the coil spring to the core wire cannot be sufficiently ensured.

If the length of the distal-end stiff portion exceeds 0.5 mm on the other hand, a shaping length (outside length ($L_{52}$)) which will be described hereinafter) cannot be set to 0.7 mm or less.

In order to set the length of the distal-end stiff portion to 0.1 to 0.5 mm in the guide wire according to the present invention, it is preferable that the coil pitch of the front end-side small-diameter portion 21 of the coil spring is 1.0 to 1.8 times as much as the wire diameter of the coil, and the Au—Sn solder penetrates into the interior of the coil in a range corresponding to 1 to 3 pitches of the coil spring.

The medical guide wire according to this embodiment has a feature in that the Au—Sn solder is used as the solder for fixing the front end-side small-diameter portion of the coil spring to the core wire.

The Au—Sn solder used in the present invention is composed of, for example, an alloy of 75-80% by mass of Au and 25 to 20% by mass of Sn.

Stainless steel is fixed to platinum (alloy) with the Au—Sn solder, whereby about 2.5 times of fixing strength (tensile strength) can be obtained compared with a case where they are fixed with the Ag—Sn solder.

Therefore, even when the length of the distal-end stiff portion is as short as 0.1 to 0.5 mm (when the penetration range of the solder is 1 to 3 times as much as the coil pitch), the fixing strength of the coil spring 20 to the core wire 10 can be made sufficiently high. Specifically, the fixing strength can be made higher than tensile break strength at the distal end-side small-diameter portion 11 of the core wire 10. Therefore, even when tensile force is applied between the coil spring 20 and the core wire 10, the core wire 10 can be prevented from being pulled out from the coil spring.

In addition, the Au—Sn solder is excellent in contrasting characteristic for X-ray compared with the Ag—Sn solder.

Further, the Au—Sn solder is also excellent in corrosion resistance to blood and body fluid compared with the Ag—Sn solder.

As illustrated in FIG. 1 and FIG. 3(B), a rear end portion of the tapered portion 22 that is an intermediate portion of the coil spring 20 is fixed to the core wire 10 by Au—Sn solder 32.

In short, the Au—Sn solder 32 penetrates into the interior of the rear end portion of the tapered portion 22 and comes into contact with the outer periphery of the core wire 10 (distal end-side small-diameter portion 11), whereby the rear end portion of the tapered portion 22 is fixed to the core wire 10 (distal end-side small-diameter portion 11).

As illustrated in FIG. 1 and FIG. 3(C), the rear end portion of the rear end-side large-diameter portion 23 that is the rear end portion of the coil spring 20 is fixed to the core wire 10 by Ag—Sn solder 33.

In short, the Ag—Sn solder 33 penetrates into the interior of the rear end portion (rear end portion of the rear end-side large-diameter portion 23) of the coil spring 20 and comes into contact with the outer periphery of the core wire 10 (distal end-side small-diameter portion 11), whereby the rear end portion of the coil spring 20 is fixed to the core wire 10 (distal end-side small-diameter portion 11).

Since the outside diameter of the portion, to which the rear end-side large-diameter portion 23 of the coil spring 20 is fixed, in the distal end-side small-diameter portion 11 of the core wire 10 is larger (relatively larger in fixing area) than the outside diameter of the portion (distal end), to which the front end-side small-diameter portion 21 of the coil spring 20 is fixed, the Ag—Sn solder low in fixing ability compared with the Au—Sn solder can be used.

Figure 3:
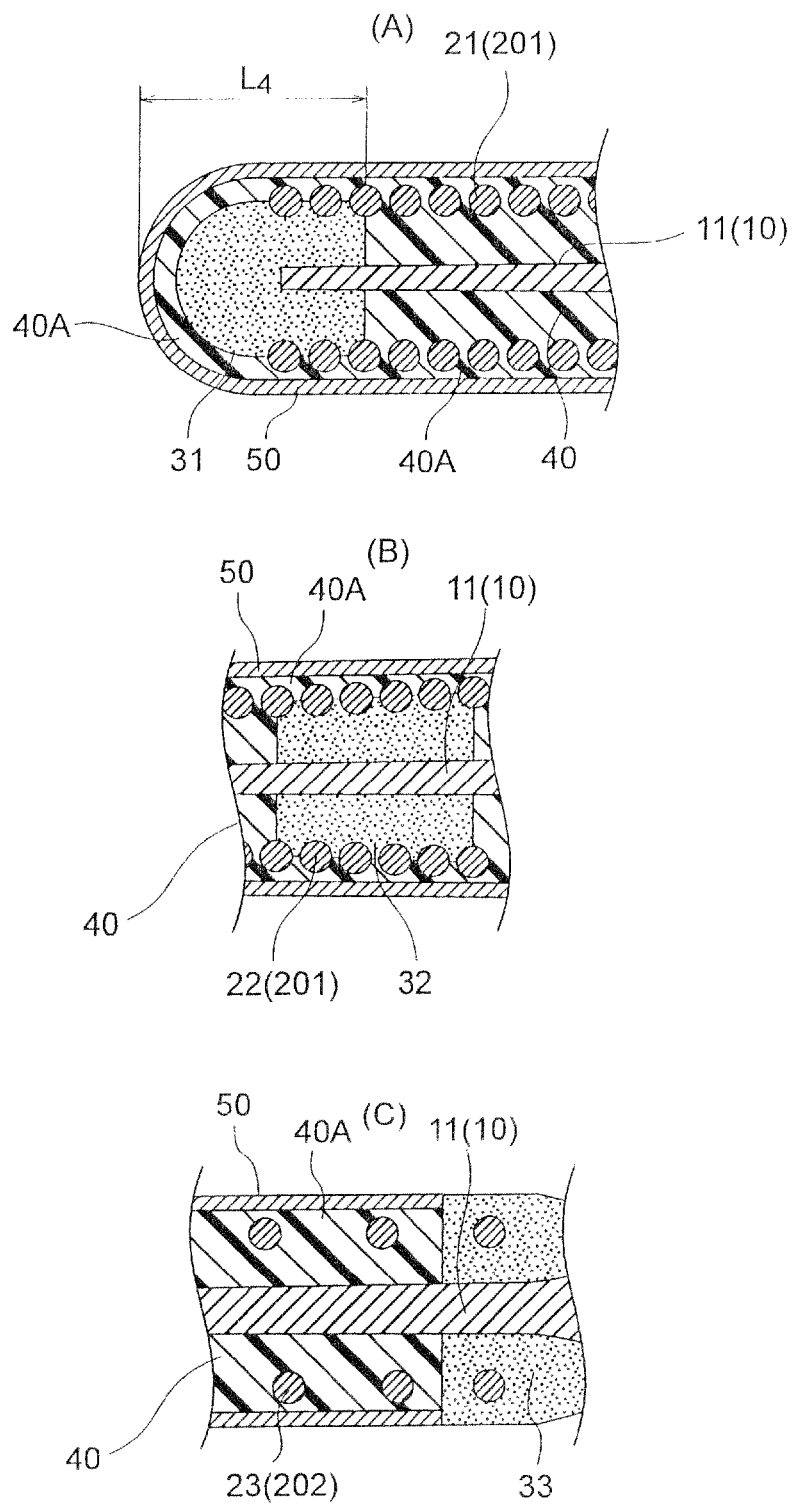
FIG. 3 is a partly enlarged view of FIG. 1, in which (A) is a detailed view of an A portion, (B) is a detailed view of a B portion, and (C) is a detailed view of a C portion.
Figure 5:
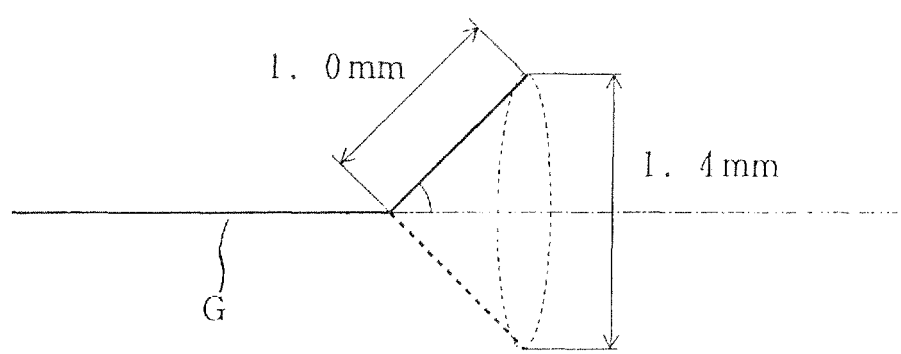
FIG. 5 is an explanatory view typically illustrating the state that the distal end portion of the guide wire has been shaped.

As illustrated in FIG. 1 to FIG. 3, in the guide wire according to this embodiment, a cured resin 40 is filled into the interior (interior into which no solder penetrates) of the coil spring 20, and the outer periphery of the coil spring 20 and the distal end tip are covered with a resin layer 40A by this cured resin 40.

A hydrophilic resin layer 50 is laminated and formed on the surface of this resin layer 40A.

The cured resin 40 is filled into the interior of the coil spring 20, whereby the integrity (interlock capability) of the core wire 10 with the coil spring 20 is especially improved. The torque transmissibility of the guide wire can be thereby improved further, and so rotational torque transferred from the proximal end-side large-diameter portion 14 of the core wire 10 is surely transferred to the distal end of the coil spring 20 integrated with the distal end-side small-diameter portion 11.

In addition, the hydrophilic resin layer 50 is formed on the outer periphery of the coil spring 20 through the resin layer 40A (primer layer), so that this hydrophilic resin layer 50 can be firmly fixed to stably develop the lubricating ability by the hydrophilic resin.

Here, the cured resin 40 filled into the interior of the coil spring 20 and forming the resin layer 40A covering the outer periphery of the coil spring 20 preferably has good adhesive property to both coil spring 20 and hydrophilic resin, and specifically, may be mentioned cured products of photo-setting resins or thermosetting resins such as urethane-acrylate resins, polyurethane resins, silicone resins, epoxy resins, acrylic resins and nylon resins.

The film thickness of the resin layer 40A covering the outer periphery of the coil spring 20 and the distal end tip is, for example, 1 to 100 μm, preferably 3 to 10 μm.

As a resin forming the hydrophilic resin layer 50 laminated and formed on the surface of the resin layer 40A, may be used all resins used in the field of medical instruments.

The film thickness of the hydrophilic resin layer 50 is, for example, 1 to 30 μm, preferably 3 to 19 μm.

As examples of a method for filling the cured resin 40 and forming the resin layer 40A and a method for laminating and forming the hydrophilic resin layer 50, may be mentioned a method of immersing the coil spring 20 installed on the core wire 10 in a curable resin, thereby filling the curable resin into the interior of the coil spring 20 and forming a resin layer on the surface of the coil spring 20, and thermosetting or photo-setting this resin to form the cured resin 40 (resin layer 40A), and then applying a hydrophilic resin to the surface of the resin layer 40A by a proper means.

The outer periphery of the tapered portion 22 of the coil spring 20 is covered with the resins (resin layer 40A and hydrophilic resin layer 50), whereby a taper as a form of the guide wire is formed.

Here, a starting point of this taper is located on a distal end-side (position indicated by $T_1$ in FIG. 2) rather than the front end of the tapered portion 22, and an end point thereof is located on a proximal end-side (position indicated by $T_2$ in FIG. 2) rather than the rear end of the tapered portion 22. In short, the taper angle of the taper as the form of the guide wire is smaller than that of the tapered portion 22, and the taper length ($L_5$) thereof is longer than the length ($L_{22}$) of the tapered portion 22.

The tapered portion 22 is covered with the resins as described above, whereby the taper form of the guide wire is made gentler than the taper of the tapered portion 22, and so an insertion operation of the guide wire can be more smoothly conducted.

When the length ($L_{22}$) of the tapered portion 22 in FIG. 2 is, for example, about 1.5 mm, the taper length ($L_5$) of the guide wire is preferably about 5 to 6 mm.

According to the guide wire of this embodiment, the Au—Sn solder is used as the solder for fixing the front end portion (front end portion of the front end-side small-diameter portion 21) of the coil spring 20 to the core wire 10, so that the fixing strength of the coil spring to the core wire (distal end-side small-diameter portion 11) is sufficiently high though the length of the distal-end stiff portion is as short as 0.3 to 0.4 mm, and so the core wire 10 is not pulled out from the coil spring 20 even when tensile force is applied between the coil spring 20 and the core wire 10.

In addition, the shaping length can be shortened because the length of the distal-end stiff portion is as short as 0.3 to 0.4 mm. As a result, frictional resistance upon operation within a micro-channel can be sufficiently reduced. In addition, a treatment in a narrow region, which has been unable to be conducted by using the conventional guide wire, also becomes feasible.

Further, the outside diameter ($D_{21}$) of coil at the front end-side small-diameter portion 21 of the coil spring 20 is as fine as 0.012 inch or less, whereby the operability upon accessing a micro-channel (for example, lubricating ability in the micro-channel) is made excellent.

Furthermore, the outside diameter ($D_1$) of the proximal end-side large-diameter portion 14 of the core wire 10 and the outside diameter ($D_{23}$) of coil of the rear end-side large-diameter portion 23 are each 0.014 inch or more, whereby sufficient flexural rigidity (pushability upon insertion, delivery performance for device after insertion) is imparted to the guide wire, and this guide wire (guide wire according to this embodiment) becomes excellent in torque transmissibility.

In addition, the cured resin 40 is filled into the interior of the coil spring 20, whereby the integrity (interlock capability) of the core wire 10 with the coil spring 20 can be improved to improve the torque transmissibility and operability of the guide wire further.

Furthermore, the hydrophilic resin layer 50 is laminated and formed on the outer periphery of the coil spring 20 through the resin layer 40A by the cured resin 40, so that the lubricating ability by the hydrophilic resin can be stably developed.

In addition, the coil spring 20 is composed of the front end-side densely-coiled portion 201 forming the front end-side small-diameter portion 21 and the tapered portion 22, and the rear end-side roughly-coiled portion 202 forming the rear end-side large-diameter portion 23, so that good contrasting characteristic for X-ray (visibility) can be developed at the front end-side small-diameter portion 21 and the tapered portion 22, which are formed by the front end-side densely-coiled portion 201.

FIG. 4(A) illustrate a state that the distal end portion of the guide wire, the outside diameter of coil of the front end-side small-diameter portion of which is 0.010 inch, according to the present invention has been shaped. The length of the distal-end stiff portion of this guide wire is 0.35 mm (the penetration range of the Au—Sn solder corresponding to 2 pitches of the coil spring), and the shaping length is 0.32 mm for inside length ($L_{51}$) and 0.53 mm for outside length ($L_{52}$).

FIG. 4(B) illustrate a state that the distal end portion of the conventional guide wire, the outside diameter of coil of the coil spring of which is 0.010 inch, has been shaped. The length of the distal-end stiff portion of this guide wire is 0.8 mm (the penetration range of the Ag—Sn solder corresponding to 6 pitches of the coil spring), and the shaping length is 0.82 mm for inside length ($L_{51}$) and 1.01 mm for outside length ($L_{52}$).

The embodiment that the Au—Sn solder is used as the solder for fixing the front end portion (front end portion of the front end-side small-diameter portion) and intermediate portion (rear end portion of the tapered portion) of the coil spring to the core wire has been described above. However, the same effect as in the case where the Au—Sn solder is used can be exhibited even by using other gold-containing solder in place of the Au—Sn solder.

As examples of other gold-containing solder than the Au—Sn, may be mentioned Au alloy solder such as Au—Ge solder, Au—Si solder, Au—In solder and Au—Sb solder, and Au solder.

EXAMPLES

Example 1

(1) Preparation of Guide Wire

A coil spring was installed on a distal end-side small-diameter portion of a core wire (core wire composed of stainless steel coated with PTFE) the outside diameter of a proximal end-side large-diameter portion of which was 0.014 inch to prepare 6 guide wires of such a structure as illustrated in FIG. 1 to FIG. 3 according to the present invention.

Here, the coil springs 20 used were such that a front end-side small-diameter portion 21 and a tapered portion 22 are formed by a front end-side densely-coiled portion 201 (the coil pitch is about 1.3 times as much as the wire diameter of the coil), a rear end-side large-diameter portion 23 is formed by a rear end-side roughly-coiled portion 202 (the coil pitch is about 3.0 times as much as the wire diameter of the coil), the length ($L_2$) is 165 mm, the outside diameter ($D_{21}$) of coil at the front end-side small-diameter portion 21 is 0.010 inch, the length ($L_{21}$) thereof is 38.5 mm, the outside diameter ($D_{23}$) of coil at the rear end-side large-diameter portion 23 is 0.014 inch, the length ($L_{23}$) thereof is 125 mm, and the length ($L_{22}$) of the tapered portion 22 is 1.5 mm.

In addition, a front end portion (front end portion of the front end-side small-diameter portion 21) and an intermediate portion (rear end portion of the tapered portion 22) of the coil spring 20 were fixed to the core wire with Au—Sn solder, and a rear end portion (rear end portion of the rear end-side large-diameter portion 23) of the coil spring was fixed to the core wire with Ag—Sn solder.

In each of the 6 guide wires, the number (in Table 1, abbreviated as "Number of pitches") of pitches at a coil portion corresponding to a region (length) where the solder penetrated into the interior thereof was set to any of 1 to 3. The length of a distal-end stiff portion is thereby as shown in Table 1.

In addition, after the coil spring was installed on the core wire, a cured resin (urethane-acrylate resin) was filled into the interior of the coil spring, a resin layer by the cured resin was formed on an outer periphery of the coil spring, and a hydrophilic resin layer composed of polyethylene oxide was laminated and formed on the surface of this resin layer.

(2) Evaluation of Guide Wire

With respect to each of the 6 guide wires obtained in the above item (1), a minimum shaping length (minimum length capable of being bent) was measured.

The measurement of the minimum shaping length was conducted on an inside length ($L_{51}$) and an outside length ($L_{52}$) as illustrated in FIG. 4.

In addition, tensile force was applied between the coil spring and the core wire to observe a broken site, thereby evaluating the fixing ability of the coil spring to the core wire. With respect to the evaluation standard, the guide wires were ranked as "A" where breaking occurred at the distal end-side small-diameter portion of the core wire or "B" where separation occurred between the coil spring or the distal end-side small-diameter portion and the solder. If there is even one guide wire which was ranked as "B", their guide wires cannot be provided as products. The results are shown collectively in Table 1.

TABLE 1

|  | Run No. | Kind of solder used in fixing of front end portion and intermediate portion | Number of pitches | Length of distal-end stiff portion [mm] | Minimum shaping length [mm] | | Evaluation of fixing ability |
|---|---|---|---|---|---|---|---|
|  |  |  |  |  | Inside length ($L_{51}$) | Outside length ($L_{52}$) |  |
| Example 1 | 1 | Au—Sn | 2 | 0.3-0.4 | 0.32 | 0.44 | A |
|  | 2 | Au—Sn | 2 | 0.3-0.4 | 0.34 | 0.47 | A |
|  | 3 | Au—Sn | 1 | 0.1-0.3 | 0.15 | 0.36 | A |
|  | 4 | Au—Sn | 3 | 0.4-0.5 | 0.43 | 0.52 | A |
|  | 5 | Au—Sn | 3 | 0.4-0.5 | 0.44 | 0.53 | A |
|  | 6 | Au—Sn | 1 | 0.1-0.3 | 0.16 | 0.35 | A |

Example 2

Six guide wires of such a structure as illustrated in FIG. 1 to FIG. 3 according to the present invention were prepared in the same manner as in Example 1 except that Au—Ge solder was used as the solder for fixing the front end portion and intermediate portion of the coil spring to the core wire, and Ag—Sn solder was used as the solder for fixing the rear end portion of the coil spring to the core wire.

In each of the 6 guide wires, the number (in Table 2, abbreviated as "Number of pitches") of pitches at a coil portion corresponding to a region (length) where the solder penetrated into the interior thereof was set to any of 1 to 3. The length of a distal-end stiff portion is thereby as shown in Table 2.

In addition, after the coil spring was installed on the core wire, in the same manner as in Example 1, the cured resin was filled into the interior of the coil spring, the resin layer by the cured resin was formed on an outer periphery of the coil spring, and the hydrophilic resin layer was laminated and formed on the surface of this resin layer.

With respect to each of the 6 guide wires obtained in the above-described manner, a minimum shaping length was measured and the fixing ability was evaluated in the same manner as in Example 1. The results are shown collectively in Table 2.

TABLE 2

|  | Run No. | Kind of solder used in fixing of front end portion and intermediate portion | Number of pitches | Length of distal-end stiff portion [mm] | Minimum shaping length [mm] | | Evaluation of fixing ability |
|---|---|---|---|---|---|---|---|
|  |  |  |  |  | Inside length ($L_{51}$) | Outside length ($L_{52}$) |  |
| Example 2 | 1 | Au—Ge | 2 | 0.3-0.4 | 0.31 | 0.43 | A |
|  | 2 | Au—Ge | 1 | 0.1-0.3 | 0.16 | 0.37 | A |
|  | 3 | Au—Ge | 3 | 0.4-0.5 | 0.43 | 0.53 | A |
|  | 4 | Au—Ge | 2 | 0.3-0.4 | 0.33 | 0.46 | A |
|  | 5 | Au—Ge | 3 | 0.4-0.5 | 0.43 | 0.53 | A |
|  | 6 | Au—Ge | 1 | 0.1-0.3 | 0.15 | 0.36 | A |

Comparative Example 1

Ag—Sn solder was used as solder for fixing the front end portion, intermediate portion and rear end portion of a coil spring to a core wire to prepare 6 comparative guide wires. In each of the 6 guide wires, the number (in Table 3, abbreviated as "Number of pitches") of pitches at a coil portion corresponding to a region (length) where the solder penetrated into the interior thereof was set to any of 1 to 3. The length of a distal-end stiff portion is thereby as shown in Table 3.

In addition, after the coil spring was installed on the core wire, in the same manner as in Example 1, the cured resin was filled into the interior of the coil spring, the resin layer by the cured resin was formed on an outer periphery of the coil spring, and the hydrophilic resin layer was laminated and formed on the surface of this resin layer.

With respect to each of the 6 guide wires obtained in the above-described manner, a minimum shaping length was measured and the fixing ability was evaluated in the same manner as in Example 1. The results are shown collectively in Table 3.

This Comparative Example 1 is a comparative example where no gold-containing solder was used upon fixing the front end portion of the coil spring to the core wire.

TABLE 3

| | Run No. | Kind of solder used in fixing of front end portion and intermediate portion | Number of pitches | Length of distal-end stiff portion [mm] | Minimum shaping length [mm] | | Evaluation of fixing ability |
|---|---|---|---|---|---|---|---|
| | | | | | Inside length ($L_{51}$) | Outside length ($L_{52}$) | |
| Comparative Example 1 | 1 | Ag—Sn | 2 | 0.3-0.4 | 0.33 | 0.44 | A |
| | 2 | Ag—Sn | 1 | 0.1-0.3 | 0.16 | 0.34 | B |
| | 3 | Ag—Sn | 1 | 0.1-0.3 | 0.14 | 0.33 | B |
| | 4 | Ag—Sn | 2 | 0.3-0.4 | 0.34 | 0.45 | B |
| | 5 | Ag—Sn | 3 | 0.4-0.5 | 0.45 | 0.55 | A |
| | 6 | Ag—Sn | 3 | 0.4-0.5 | 0.46 | 0.57 | B |

Comparative Examples 2 to 6

Ag—Sn solder was used as all solders for fixing the front end portion, intermediate portion and rear end portion of a coil spring to a core wire to prepare comparative guide wires the lengths of distal-end stiff portions of which exceeded 0.5 mm.

In each of the guide wires, the number (in Table 4, abbreviated as "Number of pitches") of pitches at a coil portion corresponding to a region (length) where the solder penetrated into the interior thereof was set to any of 4 to 8. The length of a distal-end stiff portion is thereby as shown in Table 4.

In addition, after the coil spring was installed on the core wire, in the same manner as in Example 1, the cured resin was filled into the interior of the coil spring, the resin layer by the cured resin was formed on an outer periphery of the coil spring, and the hydrophilic resin layer was laminated and formed on the surface of this resin layer.

With respect to each of the guide wires obtained in the above-described manner, a minimum shaping length was measured in the same manner as in Example 1. The results are shown collectively in Table 4.

TABLE 4

| | Kind of solder used in fixing of front end portion and intermediate portion | Number of pitches | Length of distal-end stiff portion [mm] | Minimum shaping length [mm] | |
|---|---|---|---|---|---|
| | | | | Inside length ($L_{51}$) | Outside length ($L_{52}$) |
| Comp. Ex. 2 | Ag—Sn | 4 | 0.6-0.7 | 0.64 | 0.77 |
| Comp. Ex. 3 | Ag—Sn | 5 | 0.7-0.8 | 0.76 | 0.87 |
| Comp. Ex. 4 | Ag—Sn | 6 | 0.8-0.9 | 0.84 | 1.02 |
| Comp. Ex. 5 | Ag—Sn | 7 | 0.9-1.0 | 0.95 | 1.08 |
| Comp. Ex. 6 | Ag—Sn | 8 | 1.0-1.1 | 1.06 | 1.17 |

Examples 3 to 5

Any of Au—Si solder, Au—In solder and Au—Sb solder was used as the solder for fixing the front end portion and intermediate portion of a coil spring to a core wire, and Ag—Sn solder was used as the solder for fixing the rear end portion of the coil spring to the core wire, thereby preparing 9 guide wires (3 guide wires in each Example) according to the present invention. In each of the guide wires thus obtained, the number (in Table 5, abbreviated as "Number of pitches") of pitches at a coil portion corresponding to a region (length) where the solder penetrated into the interior thereof was set to any of 1 to 3. The length of a distal-end stiff portion is thereby as shown in Table 5.

In addition, after the coil spring was installed on the core wire, in the same manner as in Example 1, the cured resin was filled into the interior of the coil spring, the resin layer by the cured resin was formed on an outer periphery of the coil spring, and the hydrophilic resin layer was laminated and formed on the surface of this resin layer.

With respect to each of the 9 guide wires obtained in the above-described manner, a minimum shaping length was measured and the fixing ability was evaluated in the same manner as in Example 1. The results are shown collectively in Table 5.

TABLE 5

| | Kind of solder used in fixing of front end portion and intermediate portion | Number of pitches | Length of distal-end stiff portion [mm] | Minimum shaping length [mm] | | Evaluation of fixing ability |
|---|---|---|---|---|---|---|
| | | | | Inside length ($L_{51}$) | Outside length ($L_{52}$) | |
| Ex. 3 | Au—Si | 1 | 0.1-0.3 | 0.16 | 0.37 | A |
| | Au—Si | 2 | 0.3-0.4 | 0.32 | 0.45 | A |
| | Au—Si | 3 | 0.4-0.5 | 0.43 | 0.53 | A |

TABLE 5-continued

| | Kind of solder used in fixing of front end portion and intermediate portion | Number of pitches | Length of distal-end stiff portion [mm] | Minimum shaping length [mm] Inside length ($L_{51}$) | Minimum shaping length [mm] Outside length ($L_{52}$) | Evaluation of fixing ability |
|---|---|---|---|---|---|---|
| Ex. 4 | Au—In | 1 | 0.1-0.3 | 0.15 | 0.36 | A |
| | Au—In | 2 | 0.3-0.4 | 0.34 | 0.47 | A |
| | Au—In | 3 | 0.4-0.5 | 0.44 | 0.53 | A |
| Ex. 5 | Au—Sb | 1 | 0.1-0.3 | 0.16 | 0.38 | A |
| | Au—Sb | 2 | 0.3-0.4 | 0.33 | 0.46 | A |
| | Au—Sb | 3 | 0.4-0.5 | 0.43 | 0.52 | A |

REFERENCE NUMERALS LIST

10 Core wire
11 Distal end-side small-diameter portion
13 Tapered portion
14 Proximal end-side large-diameter portion
20 Coil spring
21 Front end-side small-diameter portion
22 Tapered portion
23 Rear end-side large-diameter portion
201 Front end-side densely-coiled portion
202 Rear end-side roughly-coiled portion
31 Au—Sn solder
32 Au—Sn solder
33 Ag—Sn solder
40 Cured resin
40A Resin layer
50 Hydrophilic resin layer
60 Water-repellent resin layer

The invention claimed is:

1. A medical guide wire comprising:
(a) a core wire having (i) a distal end-side small-diameter portion and (ii) a proximal end-side large-diameter portion, the proximal end-side large-diameter portion having an outside diameter that is larger than an outside diameter of the distal end-side small-diameter portion, and
(b) a coil spring made of a single piece of wire material, the coil spring being installed on an outer periphery of the distal end-side small-diameter portion of the core wire along an axial direction throughout an entire length of the coil spring, the coil spring having (i) a coiled front end-side small-diameter portion having a coil formed by winding the wire material plural times spirally, the coil of the coiled front end-side small-diameter portion having a fixed outside diameter, (ii) a coiled rear end-side large-diameter portion having a coil formed by winding the wire material plural times spirally, the coil of the coiled rear end-side large-diameter portion having a fixed outside diameter that is larger than the fixed outside diameter of the coil of the coiled front end-side small-diameter portion, and (iii) a coiled tapered portion formed by winding the wire material plural times spirally, the coiled tapered portion being located between the front end-side small-diameter portion and the rear end-side large-diameter portion, and the coil spring being fixed to the core wire at least at a front end portion of the front end-side small-diameter portion and a rear end portion of the rear end-side large-diameter portion, wherein
the front end-side small-diameter portion of the coil spring has a length of 5 to 100 mm, and the outside diameter of the coil thereof is at most 0.012 inch,
the rear end-side large-diameter portion of the coil spring has a length of 85 to 154.5 mm, and the tapered portion of the coil spring has a length of 0.5 to 10 mm,
an outside diameter of the wire material forming the coil spring is 30 to 90 μm,
the front end portion of the front end-side small-diameter portion of the coil spring is fixed to the core wire by a gold-containing solder selected from the group consisting of a Au—Si solder, a Au—In solder and a Au—Sb solder,
a length of a distal end portion stiffened by the gold-containing solder is 0.1 to 0.5 mm,
the coil spring is composed of a front end-side densely-coiled portion whose coil pitch is 1.0 to 1.8 times as much as the outside diameter of the wire material, and a rear end-side roughly-coiled portion whose coil pitch is 1.8 to 3.0 times as much as the wire diameter of the coil,
the front end-side small-diameter portion and the tapered portion are formed by the front end-side densely-coiled portion of the coil spring, and the rear end-side large-diameter portion is formed by the rear end-side roughly-coiled portion of the coil spring, and
the coil spring being fixed to the core wire at a rear end portion of the tapered portion that is an intermediate portion of the coil spring by the gold-containing solder.

2. A medical guide wire comprising:
(a) a core wire having (i) a distal end-side small-diameter portion and (ii) a proximal end-side large-diameter portion, the proximal end-side large-diameter portion having an outside diameter that is larger than an outside diameter of the distal end-side small-diameter portion, and
(b) a coil spring made of a single piece of wire material, the coil spring being installed on an outer periphery of the distal end-side small-diameter portion of the core wire along an axial direction throughout an entire length of the coil spring, the coil spring having (i) a coiled front end-side small-diameter portion having a coil formed by winding the wire material plural times spirally, the coil of the coiled front end-side small-diameter portion having a fixed outside diameter, (ii) a coiled rear end-side large-diameter portion having a coil formed by winding the wire material plural times spirally, the coil of the coiled rear end-side large-diameter portion having a fixed outside diameter that is larger than the fixed outside diameter of the coil of the coiled front end-side small-diameter portion, and (iii) a coiled tapered portion formed by winding the wire material plural times spirally, the coiled tapered portion being located between the front end-side small-diameter portion and the rear end-side large-diameter portion, and the coil spring being fixed to the core wire at least at a front end portion of the front end-side small-diameter portion and a rear end portion of the rear end-side large-diameter portion, wherein
the front end-side small-diameter portion of the coil spring has a length of 5 to 100 mm, and the outside diameter of the coil thereof is at most 0.012 inch,
the rear end-side large-diameter portion of the coil spring has a length of 85 to 154.5 mm, and the tapered portion of the coil spring has a length of 0.5 to 10 mm,
an outside diameter of the wire material forming the coil spring is 30 to 90 μm, the front end portion of the front end-side small-diameter portion of the coil spring is fixed to the core wire by a Au—Sn solder, a length of a distal end portion stiffened by the Au—Sn solder is 0.1 to 0.5 mm, the coil spring is composed of a front end-side densely-coiled portion whose coil pitch is 1.0 to 1.8 times as much as the outside diameter of the wire material, and a rear end-side roughly-coiled portion whose coil pitch is 1.8 to 3.0 times as much as the wire diameter of the coil, the front end-side small-diameter portion and the tapered portion are formed by the front end-side densely-coiled portion of the coil spring, and the rear end-side large-diameter portion is formed by the rear end-side roughly-coiled portion of the coil spring, and the coil spring being fixed to the core wire at a rear end portion of the tapered portion that is an intermediate portion of the coil spring by the Au—Sn solder.

3. The medical wire according to claim 2, wherein the outside diameter of the coil of the front end-side small-diameter portion of the coil spring is at most 0.010 inch.

4. The medical guide wire according to claim 3, wherein the outside diameter of the proximal end-side large-diameter portion of the core wire and the outside diameter of the coil of the rear end-side large-diameter portion of the coil spring are each at least 0.014 inch.

5. The medical guide wire according to claim 2, wherein the Au—Sn solder penetrates into an interior of the coil of the coiled front end-side small-diameter portion in a range corresponding to 1 to 3 pitches of the coil spring.

6. The medical guide wire according to claim 2, further comprising a resin layer formed on an outer periphery of the coil spring, a hydrophilic resin layer laminated and formed on a surface of the resin layer, and a water-repellent resin layer formed on a surface of the core wire.

7. The medical guide wire according to claim 2, wherein the core wire is composed of stainless steel.

8. A medical guide wire comprising:
(a) a core wire having (i) a distal end-side small-diameter portion and (ii) a proximal end-side large-diameter portion, the proximal end-side large-diameter portion having an outside diameter that is larger than an outside diameter of the distal end-side small-diameter portion, and
(b) a coil spring made of a single piece of wire material, the coil spring being installed on an outer periphery of the distal end-side small-diameter portion of the core wire along an axial direction throughout an entire length of the coil spring, the coil spring having (i) a coiled front end-side small-diameter portion having a coil formed by winding the wire material plural times spirally, the coil of the coiled front end-side small-diameter portion having a fixed outside diameter, (ii) a coiled rear end-side large-diameter portion having a coil formed by winding the wire material plural times spirally, the coil of the coiled rear end-side large-diameter portion having a fixed outside diameter that is larger than the fixed outside diameter of the coil of the coiled front end-side small-diameter portion, and (iii) a coiled tapered portion formed by winding the wire material plural times spirally, the coiled tapered portion being located between the front end-side small-diameter portion and the rear end-side large-diameter portion, and the coil spring being fixed to the core wire at least at a front end portion of the front end-side small-diameter portion and a rear end portion of the rear end-side large-diameter portion, wherein the front end-side small-diameter portion of the coil spring has a length of 5 to 100 mm, and the outside diameter of the coil thereof is at most 0.012 inch, the rear end-side large-diameter portion of the coil spring has a length of 85 to 154.5 mm, and the tapered portion of the coil spring has a length of 0.5 to 10 mm, an outside diameter of the wire material forming the coil spring is 30 to 90 µm, the front end portion of the front end-side small-diameter portion of the coil spring is fixed to the core wire by a Au—Ge solder, a length of a distal end portion stiffened by the Au—Ge solder is 0.1 to 0.5 mm, the coil spring is composed of a front end-side densely-coiled portion whose coil pitch is 1.0 to 1.8 times as much as the outside diameter of the wire material, and a rear end-side roughly-coiled portion whose coil pitch is 1.8 to 3.0 times as much as the wire diameter of the coil, the front end-side small-diameter portion and the tapered portion are formed by the front end-side densely-coiled portion of the coil spring, and the rear end-side large-diameter portion is formed by the rear end-side roughly-coiled portion of the coil spring, and the coil spring being fixed to the core wire at a rear end portion of the tapered portion that is an intermediate portion of the coil spring by the Au—Ge solder.

9. The medical guide wire according to claim 8, wherein the outside diameter of coil of the front end-side small-diameter portion of the coil spring is at most 0.010 inch.

10. The medical guide wire according to claim 9, wherein the outside diameter of the proximal end-side large-diameter portion of the core wire and the outside diameter of the coil of the rear end-side large-diameter portion of the coil spring are each at least 0.014 inch.

11. The medical guide wire according to claim 8, wherein the Au—Ge solder penetrates into an interior of the coil of the coiled front end-side small-diameter portion in a range corresponding to 1 to 3 pitches of the coil spring.

12. The medical guide wire according to claim 8, further comprising a resin layer formed on an outer periphery of the coil spring, a hydrophilic resin layer laminated and formed on a surface of the resin layer, and a water-repellent resin layer formed on a surface of the core wire.

13. The medical guide wire according to claim 8, wherein the core wire is composed of stainless steel.

* * * * *